United States Patent
Kandeel

(10) Patent No.: US 11,806,358 B1
(45) Date of Patent: Nov. 7, 2023

(54) METHOD OF TREATING TRYPANOSOMIASIS

(71) Applicant: KING FAISAL UNIVERSITY, Al-Ahsa (SA)

(72) Inventor: Mahmoud Kandeel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/131,729

(22) Filed: Apr. 6, 2023

(51) Int. Cl.
*A61K 31/7034* (2006.01)
*A61P 33/00* (2006.01)

(52) U.S. Cl.
CPC .......... *A61K 31/7034* (2013.01); *A61P 33/00* (2018.01)

(58) Field of Classification Search
CPC .......................... A61K 31/7034; A61P 33/00
See application file for complete search history.

(56) References Cited

U.S. PATENT DOCUMENTS

| | | |
|---|---|---|
| 2021/0386064 A1 | 12/2021 | Thomas |
| 2022/0257561 A1 | 8/2022 | Tejani |

FOREIGN PATENT DOCUMENTS

| | | |
|---|---|---|
| CA | 2847661 A1 | 2/2012 |
| EP | 2198862 A1 | 6/2010 |

OTHER PUBLICATIONS

Tasdemir et al., Antimicrobial Agents and Chemotherapy, 2006, 50(4), p. 1352-1364. (Year: 2006).*
Merillon et al. (eds.), Natural Antimicrobial Agents, 2018, Springer International Publishing, p. 163-194. (Year: 2018).*
Gunter et al., Zoonoses and Public Health, 2017, 64, p. 313-327. (Year: 2017).*
Ribeiro et al., Experimental Parasitology, 2016, 162, p. 1-6. (Year: 2016).*
Stompor et al., Molecules, 2019, 24, article 4468, 27 pages. (Year: 2019).*
Cassia Ortiz et al., "Therapeutic Effects of Citrus Flavonoids Neohesperidin, Hesperidin and Its Aglycone, Hesperetin on Bone Health", Biomolecules, Apr. 23, 2022;12(5):626.
Tabrez et al., "Hesperidin Targets Leishmania donovani Sterol C-24 Reductase to Fight against Leishmaniasis", ACS Omega 2021, 6, 12, 8112-8118.

* cited by examiner

*Primary Examiner* — Jonathan S Lau
(74) *Attorney, Agent, or Firm* — Nath, Goldberg & Meyer; Richard C. Litman

(57) ABSTRACT

Methods of treating trypanosomiasis and, particularly, methods of treating trypanosomiasis using neohesperidin dihydrochalcone. Such methods of treatment are useful in, for example, animals selected from the group consisting of cattle, sheep, pigs, goats, horses, and camels.

13 Claims, 2 Drawing Sheets

METHOD OF TREATING TRYPANOSOMIASIS

BACKGROUND

1. Field

The disclosure of the present patent application relates to methods of treating trypanosomiasis and, particularly, to methods of treating trypanosomiasis using neohesperidin dihydrochalcone.

2. Description of the Related Art

Trypanosomiasis is a devastating and fatal blood protozoal disease affecting humans and animals worldwide. The *Trypanosoma cruzi* parasite that causes Chagas disease is already present in 21 countries across Latin America and the southern United States. More than 7 million individuals are infected with Chagas disease at present, causing 10,000 deaths annually from its complications, and another 70 million are at risk of infection. Human African trypanosomiasis (HAT), often known as sleeping sickness, remains one of Africa's most dreaded and lethal diseases, affecting an estimated 70 million people across 36 nations in sub-Saharan Africa.

The safety and toxicity of many anti-trypanosomal medicines are extremely poor. New kinds of anti-trypanosomal drugs that are more effective and have lower host toxicity need to be discovered. There is an immediate need for effective, safe and cost-effective anti-trypanosomal medications because of microbial resistance to the few traditional anti-trypanosomal drugs, increasing vector resistance to insecticides, a lack of effective vaccinations and the side effects of the present drugs. For this reason, researchers are starting to look to natural products for potential antibacterial and antiprotozoal treatments.

Hesperidin and neohesperidin are natural citrus flavanone glycosides that have a wide range of therapeutic applications. Neohesperidin has anti-microbial properties and is a flavanone glycoside compound found in several citrus fruits. Neohesperidin is a 7-O-neohesperidose derivative of hesperidin. Neohesperidin is regarded as a flavor enhancer by the Flavor and Extract Manufacturers Association (FEMA) owing to its sweet taste. It has previously been shown that neohesperidin, hesperidin, and neoeriocitin-rich extracts not only boosted gut-beneficial bacteria but also demonstrated potent antibacterial action against pathogenic bacteria. With the minimum inhibitory concentration (MIC) values, the extract's antibacterial potential was comparable to that of conventional antibiotics like Gentamycin and Vancomycin. The results indicated that the neohesperidin-enriched extract had significant antimicrobial activity against both gram-positive and gram-negative bacteria at low concentrations. Similar results were also reported by using neohesperidin extract in a concentration range of 200 μg/ml to 800 μg/ml.

Apart from its effectiveness against bacteria, neohesperidin has also been studied for its antiprotozoal activity. Even though the literature available in this regard is quite limited, different studies have reported that neohesperidin has shown potential against several protozoa, like *Plasmodium falciparum*. The study indicated a high binding affinity of neohesperidin with different proteins of *plasmodium*, especially the ones regulating different growth phases of the pathogen. Toxoplasmosis, caused by *Toxoplasma gondii*, is another critical protozoal disease. Toxoplasmosis is generally an opportunistic infection, and it is more common in immuno-compromised patients, where it can cause severe encephalitis, brain damage, and even blindness. The antiprotozoal activity of neohesperidin against Toxoplasmosis was compared to that of other flavonoids and conventional medicines. The results indicate that neohesperidin was not as effective as other standard drugs or flavonoids. However, it seemed to slightly upregulate the growth of the toxoplasmosis agent. Neohesperidin was included in the extensive list of flavonoids compiled for their antiprotozoal properties.

Plant extracts containing bioactive compounds such as neohesperidin have been associated with antibacterial activity. The precise mechanism of neohesperidin's antimicrobial activity is unknown, but it has been proposed that flavonoids interfere with many bacterial mechanisms such as bacterial motility, cytoplasmic permeability, and metalloenzyme inhibition. In addition, it has been found that citrus flavonoids block the cell-to-cell signaling activity of bacteria. Regarding the antiprotozoal activity, previous research suggests that the antiprotozoal property of neohesperidin lies in its ability to bind with the pocket of Phosphate of Regenerating Liver-Protein Tyrosine Phosphatase (PfPRL-PTP). PfPRL is involved in the host invasion and is generally secreted by plasmodium-infected cells. PfPRL also co-localizes with AMA-1, and their combination is important for red blood cell (RBCs) invasion. Due to the importance of PfPRL in malarial infection, the protein is an important target for Neohesperidin therapy.

Thus, a method of treating trypanosomiasis solving the aforementioned problems is desired.

SUMMARY

The present subject matter is directed to a method of treating trypanosomiasis in a subject comprising administering a therapeutically effective amount of neohesperidin dihydrochalcone to a subject in need thereof. In an embodiment, the trypanosomiasis is caused by one or more trypanosome species selected from the group consisting of *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000. In an embodiment, the trypanosome species can cause a disease in at least one of blood and tissues of the subject. In an embodiment, the trypanosome species can cause a disease in tissues of the subject. In an embodiment, the subject is an animal selected from the group consisting of cattle, sheep, pigs, goats, horses, and camels.

In one embodiment, the present subject matter relates to a method of treating trypanosomiasis in a subject caused by a trypanosome species causing a disease in tissues. In an embodiment, the subject is an animal selected from the group consisting of cattle, sheep, pigs, goats, horses, and camels.

In a further embodiment, the present subject matter relates to a method of treating an animal for trypanosomiasis, the animal being selected from the group consisting of cattle, sheep, pigs, goats, horses, and camels. In an embodiment, trypanosomiasis is caused by a tissue trypanosome, a trypanosome species, or a trypanosome affecting tissues of the animal. In an embodiment, the animal is selected from horses and camels. In an embodiment, the animal is a horse and the trypanosome species is *T. equiperdum*. In an embodiment, the animal is a camel and the trypanosome species is *T. evansi*. In an embodiment, the trypanosome species is *T. congolense*.

DETAILED DESCRIPTION OF THE PREFERRED EMBODIMENTS

Figures 1A, 1B:
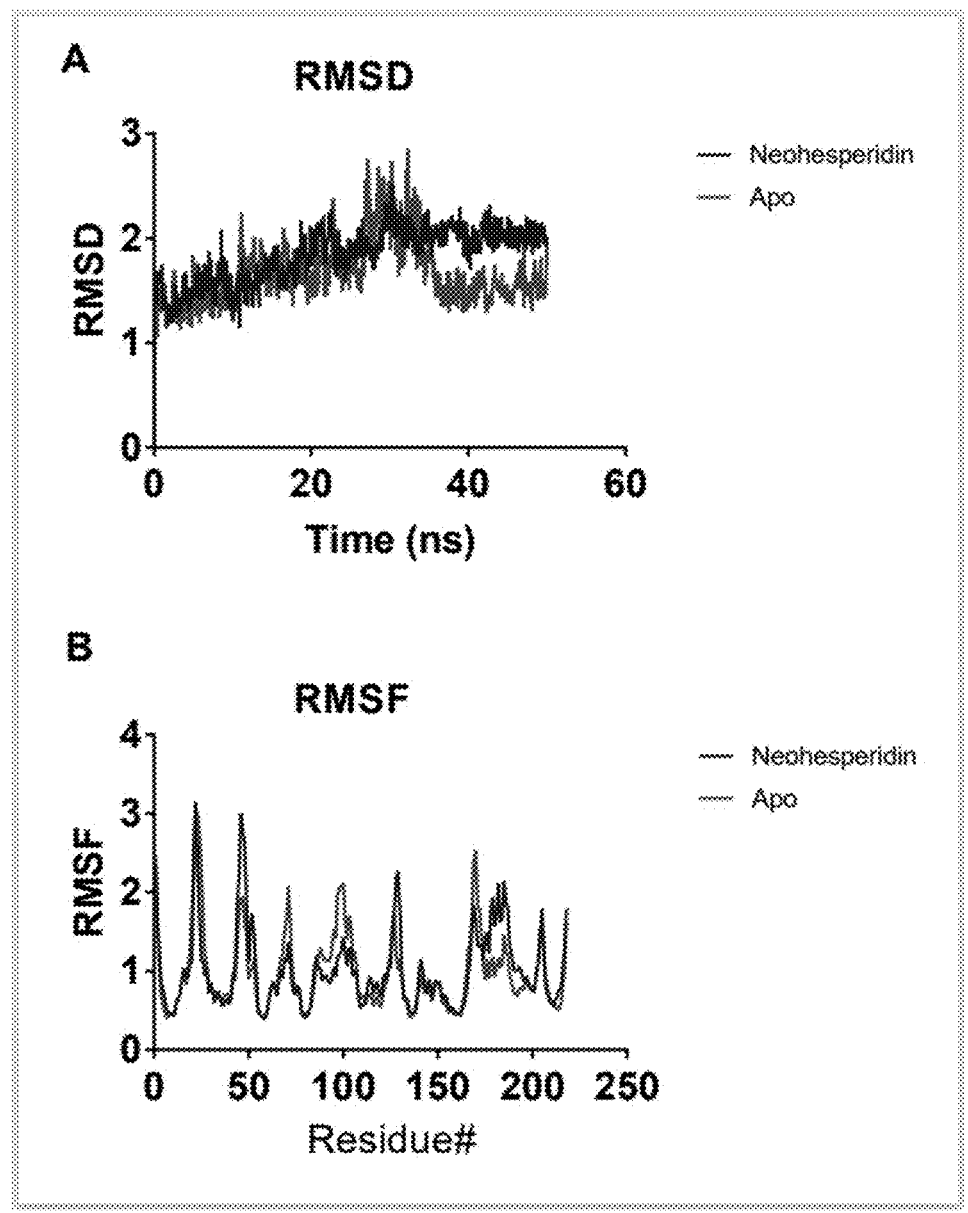
FIGS. 1A-1B are graphs showing (A) RMSD of Apo TbDHFR or bound with neohesperidin dihydrochalcone for 50 ns; and (B) RMSF of Apo TbDHFR or bound with neohesperidin dihydrochalcone for 50 ns.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter is directed to a method of treating trypanosomiasis in a subject comprising administering a therapeutically effective amount of neohesperidin dihydrochalcone to a subject in need thereof. Neohesperidin dihydrochalcone has a strong affinity for *Trypanosoma brucei* dihydrofolate reductase (TbDHFR) which is a sugar derivative of neohesperidin and an important antimicrobial and antiprotozoal target. As described herein, the binding of neohesperidin to TbDHFR was confirmed by docking and MD simulations, as demonstrated by a stable root mean square deviation (RMSD) record, low residue fluctuations, a tight radius of gyration (ROG), and an average of about 2.1±1.1 hydrogen bonds throughout a 50 ns MD simulation. A virtual screening study of neohesperidin alone with *Trypanosoma* DHFR-TS showed weak binding with the enzyme. While hesperidin had previously demonstrated good binding potency with the enzyme, hesperidin did not previously show any trypanocidal action when tested. Thus, as described herein, neohesperidin dihydrochalcone, instead of hesperidin, was tested and demonstrated broad-spectrum anti-trypanosomal action.

In an embodiment, a method of treating trypanosomiasis in a subject comprises administering a therapeutically effective amount of neohesperidin dihydrochalcone to a subject in need thereof. In a particular embodiment, trypanosomiasis is caused by one or more trypanosome species selected from the group consisting of *T. b. brucei* (TbbGUTat 3.1), *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000.

In an embodiment, the trypanosome species can cause a disease in at least one of blood and tissues of the subject. In an embodiment, the trypanosome species can cause a disease in tissues of the subject. In an embodiment, the subject is an animal selected from the group consisting of cattle, sheep, pigs, goats, horses, and camels. In an embodiment, the subject is a horse and the trypanosome species is *T. equiperdum*. In an embodiment, the trypanosome species causes equine genital trypanosomiasis. In an embodiment, the subject is a camel and the trypanosome species is *T. evansi*. In an embodiment, the trypanosome species is *T. b. gambiense*.

As described herein, neohesperidin dihydrochalcone demonstrated broad-spectrum trypanocidal activity against *Trypanosoma*. Neohesperidin dihydrochalcone showed broad-spectrum antitrypanosomal action with an IC50 range of about 8.88-22.53 μg/ml. The strongest trypanocidal activity was found on TbgIL1922 with IC50=about 8.88±3.84 μg/ml, while the TcIL3000 showed the highest resistance to the trypanosomal activity of neohesperidin dihydrochalcone with IC50=about 22.53±2.3 μg/ml.

In one embodiment, the present subject matter relates to a method of treating trypanosomiasis caused by a trypanosome species causing a disease in tissues of the subject. In an embodiment, the trypanosome species is selected from the group consisting of *T. evansi* (Tev) Tansui and *T. equiperdum* (Teq). In an embodiment, the subject is an animal selected from the group consisting of cattle, sheep, pigs, goats, horses, and camels. In an embodiment, the animal is selected from the group consisting of horses and camels. In an embodiment, the subject is a horse and the trypanosome species is *T. equiperdum*. In an embodiment, the trypanosome species causes equine genital trypanosomiasis. In an embodiment, the subject is a camel and the trypanosome species is *T. evansi*. In an embodiment, the trypanosome species is *T. b. gambiense*.

In a further embodiment, the present subject matter relates to a method of treating an animal for trypanosomiasis, the animal being selected from the group consisting of cattle, sheep, pigs, goats, horses, and camels. In an embodiment, the trypanosomiasis is caused by a tissue trypanosome or a trypanosome affecting tissues of the animal. In an embodiment, the animal is selected from the group consisting of horses and camels. In an embodiment, the animal is a horse and the trypanosome species is *T. equiperdum*. In an embodiment, the animal is a camel and the trypanosome species is *T. evansi*. In an embodiment, the trypanosome species is *T. b. gambiense*.

Traditionally, trypanocidal drugs that have been effective for inhibiting a particular species of trypanosomes, have not been effective for inhibiting other species of trypanosomes. This is generally attributed to morphological and structural distinctions between the species and holds especially true for trypansomes affecting horses and camels. T. *Equiperdum* is a species of kinetoplastid parasites that causes Dourine disease or covering sickness in horses and other animals in the family equidae. *T. equiperdum* is the only trypanosome that is not spread by an insect vector and can be transmitted through the venereal route. *T. evansi* is the broadest spectrum member of trypanosomes that infects a wide range of animal hosts. It has morphological and structural distinctions from other known trypanosomes and the discovery of specific drugs specific for this species is recommended.

Dourine disease is known for being highly resistant to treatment (Cauchard, J., D. Carnicer, A. Madeline, E. Guitton, A. Giraudet, P. Biischer, L. Hebert, and C. Laugier. "Evaluation of Melarsamine hydrochloride (Cymelarsan®) efficacy for the treatment of dourine nervous form on experimentally infected ponies." J Equine Vet Sci 39 (2016): S51.). Many trypanocidal drugs that have been used in the treatment of Dourine have shown variable results, with chronic cases being particularly unresponsive to treatment. To get effective results, repeated administration or combination of more than one drug has been required. Given that, most of the currently available anti-trypanosomal drugs have narrow safety margin. The four main drugs on the market that are used to treat the clinical signs of Dourine, namely Suramin, Diminazen, Cymerlarsan, and Quinapyramin, do not provide a cure and animals treated with these drugs typically experience relapses.

Neohesperidin dihydrochalcone can be administered at a therapeutically or pharmaceutically effective dosage, e.g., a dosage sufficient to provide treatment for trypanosomiasis. Administration of neohesperidin dihydrochalcone or pharmaceutical compositions thereof can be by any method that delivers neohesperidin dihydrochalcone systemically and/or locally. These methods include oral routes, parenteral routes, intraduodenal routes, and the like.

While dosage levels have yet to be optimized, generally, a daily dose of the neohesperidin dihydrochalcone is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing neohesperidin dihydrochalcone for treatment of trypanosomiasis, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The neohesperidin dihydrochalcone can also be administered in sustained or controlled release dosage forms, including depot injections, osmotic pumps, pills, transdermal (including electrotransport) patches, and the like, for the prolonged administration at a predetermined rate, preferably in unit dosage forms suitable for single administration of precise dosages.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the neohesperidin dihydrochalcone, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. neohesperidin dihydrochalcone and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained-release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. Percentages of neohesperidin dihydrochalcone of about 0.01% to about 10% in solution are employable and may be higher if the composition is a solid which will be subsequently diluted to the above percentages. The composition may comprise about 0.2% to about 2% of the neohesperidin dihydrochalcone in solution.

Nasal solutions of the neohesperidin dihydrochalcone alone or in combination with other pharmaceutically acceptable excipients can also be administered.

Formulations of the neohesperidin dihydrochalcone or a salt may also be administered to the respiratory tract as an aerosol or solution for a nebulizer, or as a microfine powder for insufflation, alone or in combination with an inert carrier such as lactose. In such a case, the particles of the formulation have diameters of less than about 50 microns, for example less than about 40 microns, less than about 30 microns, less than about 20 microns, or less than about 10 microns. In an embodiment, the particles of the formulation have diameters of less than about 10 microns.

The present teachings are illustrated by the following examples.

Example 1

Anti-Trypanosomal Assay

Six trypanosome species namely *T. b. brucei* (Tbb) GuTat3.1, *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000, were cultivated using HMI-9 medium and used in the study. The trypanocidal activity of hesperidin and neohesperidin dihydrochalcone, shown below, was assessed at 25 µg/ml or 0.25 µM.

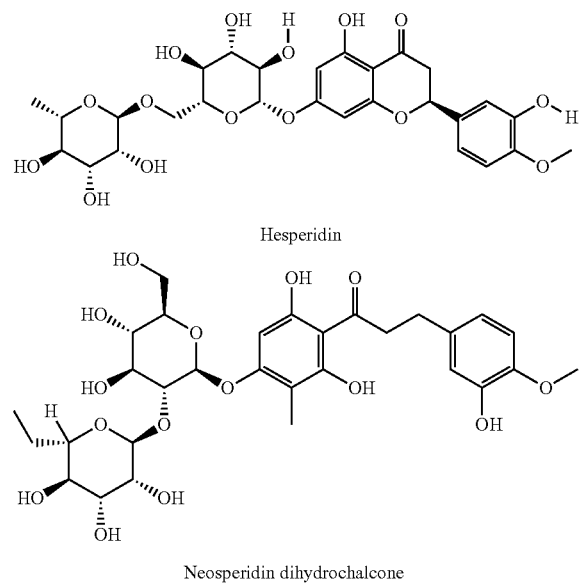

Neosperidin Dihydrochalcone

Neohesperidin dihydrochalcone showed substantial trypanocidal activity at about 25 µg/ml, while no activity was noticed for hesperidin. The IC50 of Neohesperidin dihydrochalcone against six trypanosome species was determined using serial dilution in a 96-well plate (Optical bottom plate, ThermoFisher SCIENTIFIC, MA, USA). After three days, 25 of CellTiter-Glo Luminescent cell viability reagent (Promega Corporation, WI, USA) was aliquoted into each well and luminosity was measured with a GloMax plate reader (Promega Corporation, WI, USA).

At first, hesperidin and neohesperidin dihydrochalcone were assayed at high and low concentrations of 0.25 or 25 µg/ml, respectively (Table 1). Hesperidin had inadequate antitrypanosomal activity, as evidenced by the lack or low rate of trypanocidal activity. In contrast, neohesperidin dihydrochalcone showed a broad-spectrum and strong inhibition of trypanosomal growth. At 25 µg/ml, neohesperidin dihydrochalcone suppressed all the test strains. For TcIL3000, the inhibition rate was 82.07±6.4 µg/ml, while stronger action was noticed on TbbGUTat3.1, TbrIL1501, TbgIL1922, Tev Tansui and Teq IVM-t1 by showing more than 99% inhibition rate (Table 1). At a low concentration of 0.25 µg/ml, the inhibition rate was 1.09-3.95%. Table 1 shows the inhibition rate of hesperidin and neohesperidin dihydrochalcone at 0.25 or 25 µg/ml against 6 *Trypanosoma* species, TcIL3000, TbbGUTat3.1, TbrIL1501, TbgIL1922, Tev Tansui and Teq IVM-t1.

TABLE 1

| Trypanosome | Hesperidin Inhibition rate concentration | | Neohesperidin dihydrochalcone Inhibition rate | |
|---|---|---|---|---|
| | 25 µg/ml | 0.25 µg/ml | 25 µg/ml | 0.25 µg/ml |
| TcIL3000 | 0 | 0 | 82.07 ± 6.4 | 0 |
| TbbGUTat3.1 | 1.05 ± 0.99 | 0 | 99.65 ± 0.2 | 2.89 ± 1.69 |
| TbrIL1501 | 0 | 7.17 ± 3.1 | 99.63 ± 0.25 | 3.95 ± 5.59 |
| TbgIL1922 | 0 | 1.56 ± 2.2 | 99.63 ± 0.28 | 1.09 ± 0.64 |
| Tev Tansui | 0 | 7.67 ± 5.9 | 99.18 ± 0.22 | 3.59 ± 5.5 |
| Teq IVM-t1 | 0.97 ± 1.37 | 0.015 ± 0.022 | 98.8 ± 0.17 | 0.59 ± 0.84 |

*The values are represented as (mean ± SD)

Given the promising initial anti-trypanosomal action of neohesperidin dihydrochalcone, the IC50 was measured in the presence of several commutations of the compound. Neohesperidin dihydrochalcone showed broad-spectrum anti-trypanosomal action with an IC50 range of 8.88-22.53 µg/ml (Table 2). Table 2 shows the IC50 of neohesperidin dihydrochalcone against 6 *Trypanosoma* species, TcIL3000, TbbGUTat3.1, TbrIL1501, TbgIL1922, Tev Tansui and Teq IVM-t1.

TABLE 2

| Trypanosome | Neohesperidin dihydrochalcone IC50 (µg/ml)* |
|---|---|
| TcIL3000 | 22.53 ± 2.3 |
| TbbGUTat3.1 | 11.97 ± 0.026 |
| TbrIL1501 | 9.47 ± 2.73 |
| TbgIL1922 | 8.88 ± 3.84 |
| Tev Tansui | 12.69 ± 0.98 |
| Teq IVM-t1 | 11.38 ± 3.93 |

*The values are represented as (mean ± SD)

The strongest trypanocidal activity was found on TbgIL1922 with IC50=8.88±3.84 µg/ml, while the TcIL3000 showed the highest resistance to the trypanosomal activity of neohesperidin dihydrochalcone with IC50=22.53±2.3 µg/ml. The strength of trypanocidal actions of neohesperidin dihydrochalcone was in the following order TbgIL1922>TbrIL1501>Teq IVM-t1>TbbGUTat3.1>Tev Tansui>TcIL3000.

Broad-spectrum action of neohesperidin dihydrochalcone was found on six *Trypanosoma* species.

Example 2

Molecular Docking

Neohesperidin dihydrochalcone exhibited a docking score of −3.9, compared to −4.6 for the co-crystalized ligand WR99210, which accounts for 85% of the crystallized ligand's score (Table 3). Table 3 shows the docking score and binding parameters for neohesperidin dihydrochalcone and the compound WR99210 with TbDHFR.

TABLE 3

| Title | docking score | glide hbond | glide lipo | glide evdw |
|---|---|---|---|---|
| Neohesperidin dihydrochalcone | −3.9 | −0.3 | −1.01 | −25.9 |
| compound WR99210 | −4.6 | −0.1 | −1.7 | −20.8 |

The binding of neohesperidin dihydrochalcone was supported by both favorable hydrogen bonds and lipophilic interaction scores. The hbond score for neohesperidin dihydrochalcone was −0.3, compared to −0.1 for the co-crystalized ligand. Furthermore, neohesperidin dihydrochalcone and compound WR99210 have identical lipo and evdw values. These computational factors point to the favorable binding conditions associated with neohesperidin dihydrochalcone recognition.

Inspecting the mode of binding that neohesperidin dihydrochalcone has with TbDHFR revealed that it has a favorable binding mode, which is supported by hydrogen bonds with the side chain of ILE160 and stacking interactions with PHE58. These interactions help in orienting and fixing the molecule into the active site of TbDHFR (FIG. 2).

Using the protein preparation module, the docking of the PDB 3RG9 structure was optimized. Detrimental crystallographic chemicals and surplus water molecules were removed from the solution. The protein was made protonated by the addition of polar hydrogens, and the OPLS2005 force field was used to optimize the structures and reduce the overall energy. For docking grid generation, WR99210 was employed as the center of a 20 Å grid box.

The Standard SP Glide docking approach was applied, and docking scores were used to rank the final findings. For verification, WR99210 was redocked, and when compared to the bound ligand, the docking position was found to be fully complementary and had a small root-mean-squared deviation (RMSD).

Example 3

Molecular Dynamics Simulation

The RMSD was computed for the neohesperidin dihydrochalcone-TbDHFR complex and then compared to the value for Apo TbDHFR. The root mean square deviation graph, shown in FIG. 1A, demonstrates that the structure did not change at any point during the simulation. After the beginning of the simulation, the neohesperidin dihydrochalcone-TbDHFR complex arrived at stability in a short amount of time (FIG. 1A). In comparison to the Apo structure, the RMSD analysis showed that the stability of TbDHFR was significantly improved when it was complexed with neohesperidin dihydrochalcone. The ApoDHFR went through a range of fluctuations that lasted between 25 and 30 ns before returning to its stable baseline. The neohesperidin dihydrochalcone-TbDHFR complex residues showed low RMSF, which did not exceed 3 Å (FIG. 1B). In comparison with ApoTbDHFR, the neohesperidin dihydrochalcone complex lowered the amino acid fluctuations, especially at the active site within the range of residues 60-90 and 170-190.

The RMSF values of the residues in the neohesperidin dihydrochalcone-TbDHFR complex indicated quite modest fluctuating and did not surpass 3 Å. (FIG. 1B). In comparison to ApoTbDHFR, the amino acid fluctuations were reduced by the neohesperidin complex formation. This was especially noticeable at the active site, specifically within the range of residues 60-90 and 170-190.

Figures 2A, 2B:
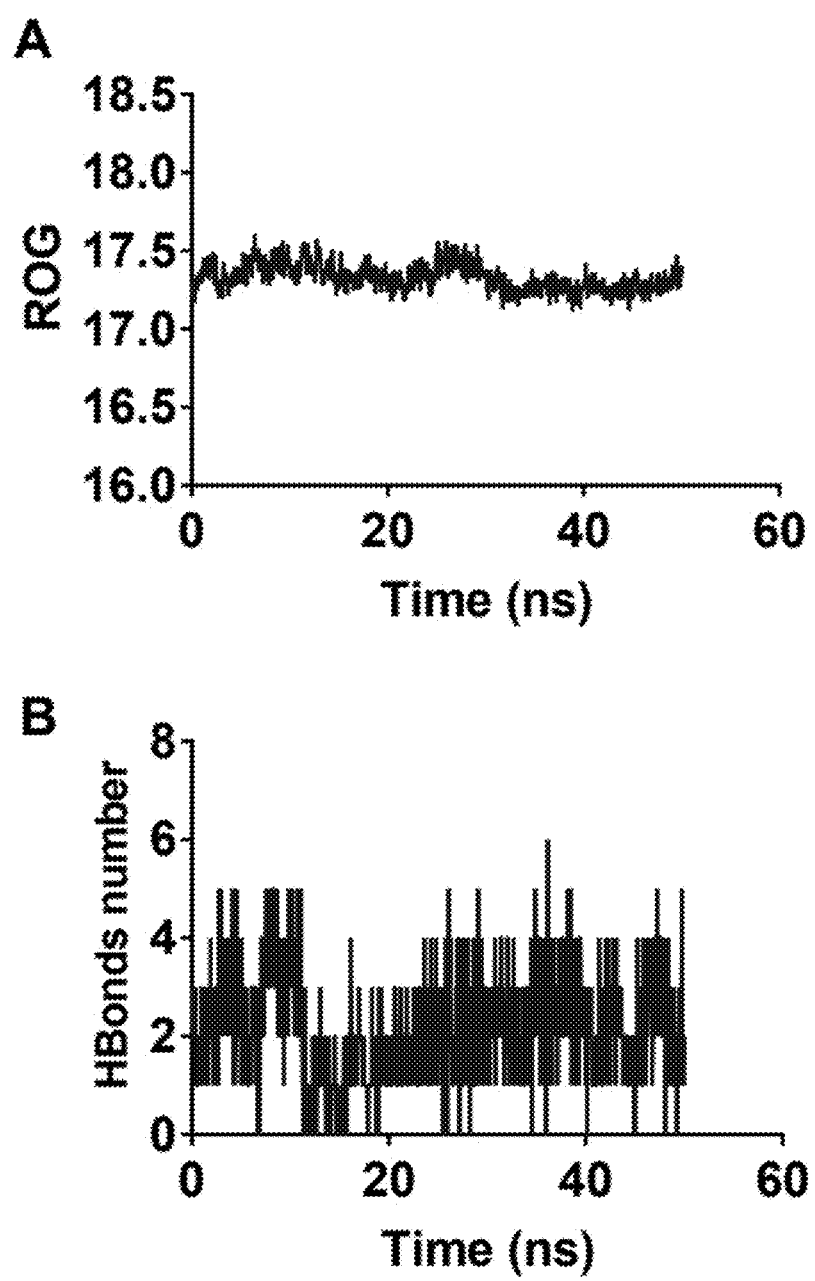
FIGS. 2A-2B are graphs showing (A) radius of gyration (ROG) of neohesperidin during simulation. B) the number of hydrogen bonds formed between neohesperidin and TbDHFR during 50 ns simulation.

The fact that there was just a marginal shift in ROG values demonstrates that the neohesperidin-TbDHFR complex is compact (FIG. 2A). During a simulation lasting 50 nanoseconds, the total number of hydrogen bonds that were formed between neohesperidin and TbDHFR was traced (FIG. 2B). According to the statistics on hydrogen bonding, the number of hydrogen bonds can range anywhere from 0 to 6, with a mean value of 2.1 and a standard deviation of 1.1. This suggests that neohesperidin has established a stable binding relationship with TbDHFR.

The antimicrobial activities of Neohesperidin-enriched cold pressed oil of grapefruit, lemon, and orange were elucidated. The study compared the antimicrobial activity of different oils to standard antibiotics (amoxicillin, ampicillin, tobramycin, piperacillin, mezlocillin, and cycloheximide) as well as standard flavonoids (Neohesperidin dihydrochalcone, hesperidin, naringin, and naringenin). The zones of inhibition experiment revealed that oils and flavonoid standards have zones of inhibition that were quite comparable to antibiotics. According to the findings of this study, Neohesperidin dihydrochalcone exhibited antiprotozoal activities. The use of computational methods uncovered the possibility of Neohesperidin dihydrochalcone forming stable complexes with TbDHFR that have a strong binding affinity. In addition, the effectiveness of Neohesperidin dihydrochalcone against six different species of *Trypanosoma* was demonstrated by trypanocidal assays.

Example 3

Statistical Analysis

MS Excel and GraphPad Prism were used to handle and show all of the data. The data were reported as Mean SD or, in some situations, as the mean plus range. Changes in each isolation parameter were expressed using descriptive statistics.

It is to be understood that the method of treating trypanosomiasis is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating trypanosomiasis in a subject, comprising:
    administering a therapeutically effective amount of neohesperidin dihydrochalcone to a subject in need thereof, wherein
    the trypanosomiasis is caused by a trypanosome species selected from the group consisting of one or more of *T. b. brucei* (TbbGUTat 3.1), *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000.

2. The method of claim 1, wherein the trypanosome species causes a disease in at least one of blood and tissues of the subject.

3. The method of claim 1, wherein the subject is an animal selected from the group consisting of cattle, sheep, pigs, goats, horses, and camels.

4. The method of claim 1, the subject is a horse and the trypanosome species is *T. equiperdum*.

5. The method of claim 1, wherein the subject is a camel and the trypanosome species is *T. evansi*.

6. The method of claim 1, wherein the trypanosome species is *T. b. gambiense*.

7. A method of treating trypanosomiasis in a subject, comprising:
    administering a therapeutically effective amount of neohesperidin dihydrochalcone to a subject in need thereof, wherein the trypanosomiasis is caused by a trypanosome species causing a disease in tissues of the subject selected from the group consisting of *T. brucei*, *T. evansi*, *Tp. equiperdum*, and *T. congolense*.

8. The method of claim 7, wherein the trypanosome species causes equine genital trypanosomiasis.

9. The method of claim 7, wherein the subject is a horse and the trypanosome species is *T. equiperdum*.

10. The method of claim 7, wherein the subject is a camel and the trypanosome species is *T. evansi*.

11. A method of treating trypanosomiasis in an animal, comprising:
    administering a therapeutically effective amount of neohesperidin dihydrochalcone to an animal in need thereof, wherein the animal is selected from the group consisting of cattle, sheep, pigs, goats, horses, and camels, wherein the trypanosomiasis is caused by a trypanosome species causing a disease in tissues of the subject selected from the group consisting of *T. brucei*, *T. evansi*, *Tp. equiperdum*, and *T. congolense*.

12. The method of claim 11, wherein the trypanosomiasis is caused by a tissue trypanosome.

13. The method of claim 11, wherein the animal is selected from the group consisting of horses and camels.

* * * * *